United States Patent [19]

Pittet et al.

[11] Patent Number: 4,694,106

[45] Date of Patent: Sep. 15, 1987

[54] METHYLTHIOIONENE DERIVATIVES AND USE THEREOF IN AUGMENTING OR ENHANCING THE AROMA OR TASTE OF FOODSTUFFS

[75] Inventors: Alan O. Pittet, Atlantic Highlands; Ranya Muralidhara, Fair Haven; Manfred H. Vock, Locust; Kevin P. Miller, Middletown; Domenick Luccarelli, Jr., Neptune, all of N.J.

[73] Assignee: International Flavors & Fragrances Inc., New York, N.Y.

[21] Appl. No.: 837,145

[22] Filed: Mar. 7, 1986

Related U.S. Application Data

[62] Division of Ser. No. 768,726, Aug. 23, 1985, Pat. No. 4,599,237.

[51] Int. Cl.$^4$ ............................................. C07C 149/26
[52] U.S. Cl. .......................................... 568/38; 568/57
[58] Field of Search ........................... 568/38, 57, 591

[56] References Cited

U.S. PATENT DOCUMENTS 3,911,028 10/1975 Sanders et al. ..................... 568/820
4,504,508 3/1985 Pittet et al. ............................ 568/57
4,548,743 10/1985 Sprecker et al. ..................... 568/591
4,565,707 1/1986 Pittet et al. ............................ 568/57

FOREIGN PATENT DOCUMENTS 544651 4/1942 United Kingdom .................. 568/57

OTHER PUBLICATIONS

B. Mikailov et al., Chem. Abstracts 60:9314h (1964), Polyene Compounds XVI, Thioketals of Unsaturated Ketones and their Transformations.

Primary Examiner—Mary E. Ceperley
Attorney, Agent, or Firm—Arthur L. Liberman

[57] ABSTRACT

Described are methylthioionene derivatives defined according to the structure:

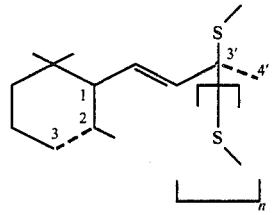

wherein n is 0 or 1; wherein the dashed lines each represent a carbon-carbon single bond or a carbon-carbon double bond with the proviso that when the dashed line at the 3′–4′ position is a double bond, n represents 0 and uses thereof in augmenting or enhancing the aroma or taste of foodstuffs.

3 Claims, 3 Drawing Figures

FIG. 2 NMR SPECTRUM FOR PEAK I OF EXAMPLE II.

FIG. 3 NMR SPECTRUM FOR PEAK 2, EXAMPLE II.

METHYLTHIOIONENE DERIVATIVES AND USE THEREOF IN AUGMENTING OR ENHANCING THE AROMA OR TASTE OF FOODSTUFFS

This is a divisional of application Ser. No. 768,726, filed Aug. 23, 1985, now U.S. Pat. No. 4,599,237.

BACKGROUND OF THE INVENTION

This invention relates to methylthioionene derivatives defined according to the structure:

wherein n is 0 or 1; wherein the dashed lines each represent a carbon-carbon single bond or a carbon-carbon double bond with the proviso that when the dashed line at the 3'-4' position is a double bond, n represents 0 and uses thereof in augmenting or enhancing the aroma or taste of foodstuffs particularly vegetable, raspberry and cabbage flavored foodstuffs.

There has been considerable work performed relating to substances which can be used to impart (modify, augment or enhance) flavors to (or in) foodstuffs. These substances are used to diminish the use of natural materials, some of which may be in short supply and to provide more uniform properties in the finished product.

Raw green bean, raw carrot, minty, raspberry and cabbage aroma and taste nuances are particularly desirable for many uses in many foodstuff flavors particularly in fresh vegetable and raspberry flavored foodstuffs.

Methyl mercapto damascone and methyl mercapto damascenone derivatives are well known for augmenting or enhancing the flavor of foodstuffs and tobaccos, for example, U.S. Pat. No. 4,209,025 issued on June 24, 1980 discloses the use of the genus of compounds having the structure:

in augmenting or enhancing the aroma or taste of tobacco or tobacco flavoring compositions, wherein the dashed line is a carbon-carbon single bond or a carbon-carbon double bond.

Raspberry flavored foodstuffs are augmented or enhanced using the compound 2-(4-hydroxy-4-methylpentyl) norbornadiene as disclosed in U.S. Pat. No. 3,911,028 issued on Oct. 7, 1975.

Thiomercaptals are disclosed to be useful in augmenting or enhancing the aroma or taste of foodstuffs in U.S Pat. No. 4,515,968 issued May 7, 1985 and U.S. Pat. No. 4,504,508 issued on Mar. 12, 1985.

Nothing in the prior art, however, discloses the methylthioionene derivatives of our invention or uses thereof in augmenting or enhancing the aroma or taste of foodstuffs.

BRIEF DESCRIPTION OF THE DRAWINGS

FIG. 1 is the NMR spectrum for the compound having the structure:

prepared according to Example I (Conditions: Field strength: 100 MHz; Solvent: CFCl$_3$).

FIG. 2 is the NMR spectrum for the compound having the structure:

prepared according to Example II (Conditions: Field strength: 100 MHz; Solvent: CFCl$_3$).

FIG. 3 is the NMR spectrum for the compound having the structure:

prepared according to Example II (Conditions: Field strength: 100 MHz; Solvent: CFCl$_3$).

THE INVENTION

The instant invention provides the genus of methylthioionene derivatives defined according to the structure:

wherein n is 0 or 1; wherein the dashed lines each represent a carbon-carbon single bond or a carbon-carbon double bond with the proviso that when the dashed line at the 3'-4' position is a double bond, n represents 0. These compounds hereinafter referred to as methylthioionene derivatives are useful in augmenting or enhancing the aroma and/or taste of foodstuffs.

Briefly, our invention contemplates augmenting or enhancing the aroma or taste of fresh vegetable, raspberry and cabbage flavored foodstuffs.

The compounds defined according to the genus:

wherein n is 0 or 1; wherein the dashed lines each represent a carbon-carbon single bond or a carbon-carbon double bond with the proviso that when the dashed line at the 3'-4' position is a double bond, n represents 0, augment or enhance raw green bean, raw carrot, minty, raspberry and cabbage aroma and taste nuances in foodstuffs as set forth, supra.

The methylthioionene derivatives of our invention defined according to the structure:

wherein n is 0 or 1; wherein the dashed lines each represent a carbon-carbon single bond or a carbon-carbon double bond with the proviso that when the dashed line at the 3'-4' position is a double bond, n represents 0, may be prepared by reacting α-ionone or an α-dihydro ionone generically shown by the structure:

wherein the dashed line at the 1'-2' position represents a carbon-carbon single bond or a carbon-carbon double bond. Such α-ionones or α-dihydro ionones may be reacted with methyl mercaptan to form the methylthioionene derivatives of our invention according to the reaction:

More specifically, when the reaction of the methyl mercaptan takes place with α-methyl ionone itself the product of the reaction is, in fact, two compounds having the structures:

with α-ionone having the structure:

This reaction is as follows:

On the other hand, when the reaction takes place with the dihydro-α-ionone having the structure:

one product is formed having the structure:

and this reaction is as follows:

When the reaction is carried out with α-ionone having the structure:

and the two products are formed having the structures:

these two products can be separated by means of preparative GLC (a chromatographic separation) whereby the compounds having the structures:

can be isolated in their pure forms.

The reaction:

to form the methylthioionene derivatives of our invention takes place in the presence of a protonic acid catalyst such as paratoluene sulfonic acid, xylene sulfonic acid, methane sulfonic acid, phosphoric acid and concentrated sulfuric acid. The reaction takes place in the presence of a solvent having a boiling point such that the reaction can proceed in a reasonable period of time, e.g., 1-12 hours, at atmospheric pressure or pressures somewhat greater than atmospheric pressure (up to about 10 atmospheres). The reaction temperature may vary between about 0° C. and about 140° C. Reaction temperatures greater than 140° C. give rise to unnecessary breakdown of reaction product. Reaction temperatures lower than 0° C. give rise to too long a period of time of reaction. The solvents utilized must be inert to the reaction product as well as inert to the reactants. The solvent utilized must have a boiling point of between room temperature, e.g., 25° C. and 150° C. The reaction solvent must be capable of being completely removed from the reaction product on distillation in view of the fact that the reaction products are used as food flavors for internal consumption. Accordingly, suitable solvents are, for example, cyclohexane, cyclopentane, cyclooctane, 1-methylcyclohexane, 1,2-dimethylcyclohexane, 1,2,4-trimethylcyclohexane, 2-ethyltetrahydrofuran, 2,5-dimethyltetrahydrofuran, methylenedichloride and the like.

The mole ratio of ionone derivative having the structure:

wherein the dashed line represents a carbon-carbon double bond or a carbon-carbon single bond to methyl mercaptan may vary from about 1:4 up to about 1:1.5 of ionone derivative:methyl mercaptan.

At the end of the reaction as stated, supra the reaction product is extracted from the reaction mass or the reaction product is washed, for example, with saturated sodium chloride. The reaction product is then distilled, preferably by means of vacuum distillation using a fractionation column. The resulting product may, if necessary and if desired be separated by means of preparative chromatographic techniques, e.g., preparative GLC.

Examples of the products of our invention and their organoleptic properties are as follows:

TABLE I

| Structure of Compound | Organoleptic Propeties |
|---|---|
| The compound having the structure: prepared according to Example I. | A raw, green bean and raw carrot aroma and taste profile at 10 ppm. |
| The compound having the structure: prepared according to Example II. | A minty and raspberry aroma and taste profile at 1 ppm. |
| The compound having the structure: | A cabbage aroma and taste profile at 2 ppm. |

TABLE I-continued

| Structure of Compound | Organoleptic Propeties |
|---|---|
|   prepared according to Example II. | |

When the methylthioionene derivatives of our invention are used as a food flavor adjuvant, the nature of the co-ingredients included with said methylthioionene derivatives in formulating the product composition will also serve to alter the organoleptic characteristics of the ultimate foodstuffs treated therewith. As used herein, in regard to flavors, the term "alter in its various forms" means "supplying or imparting flavor character or notes to otherwise bland, relatively tasteless substance or augmenting the existing flavor characteristics where a natural flavor is deficient in some regard or supplementing the existing flavor impression to modify its quality, character or taste".

As used herein, the term "foodstuff" includes both solid and liquid ingestible materials which usually do but need not have nutritional value. Thus, foodstuffs include soups, convenience foods, beverages, dairy products, candies, fruits, cereals, soft drinks, snacks and the like.

Substances suitable for use herein as co-ingredients or flavoring adjuvants are well known in the art for such use being extensively described in the relevant literature. Apart from the requirement that any such material be "ingestibly" acceptable and thus non-toxic or otherwise non-deleterious, nothing particularly critical resides in selection thereof. Accordingly, such materials which may in general be characterized as flavoring adjuvants or vehicles comprise broadly stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylated hydroxyanisole (mixture of 2 and 3 tertiary butyl-4-hydroxyanisole), butylated hydroxy toluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar agar; carrageenan; cellulose and cellulose derivatives such as carboxymethyl cellulose and methyl cellulose; natural and synthetic gums such as gum arabic, gum tragacanth, gelatine, proteinaceous materials; lipids; carbohydrates; starches pectins, and emulsifiers, e.g., mono- and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono- and diglycerides of fatty acids, lecithin, defoaming and flavor dispersing agents such as sorbitan monosterate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcumin and the like; firming agents such as aluminum sodium sulfate, calcium chloride and calcium gluconate; texturizers; anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, butyric acid, caproic acid, caprylic acid, formic acid, 2-Hexenoic acid, 3-Hexenoic acid, isobutyric acid, isovaleric acid, propionic acid, and valeric acid; Ketones and aldehydes, e.g., acetaldehyde, acetone, acetyl methyl carbinol, acrolein, diacetyl, $\beta,\beta$-Dimethylacrolein, Hexanal, 2-Hexenal, cis-3-Hexenal, 4(p-Hydroxyphenyl)- 2-butanone, $\alpha$-Ionone, $\beta$-Ionone, and 2-Pentenal; alcohols, such as 1-Butanol, trans-2-Buten-1-ol, Ethanol, Geraniol, 1-Hexanol, cis-3-Hexen-1-ol, 3-Methyl-3-buten-1-ol, 1-Pentanol, 1-Penten-3-ol; esters, such as Butyl acetate, Ethyl acetate, Ethyl butyrate, Ethyl crotonate, Ethyl propionate, 2-Hexenyl acetate, 2-Hexenyl butyrate, Hexyl acetate, Hexyl butyrate, Isoamyl acetate, Isopropyl butyrate, Methyl butyrate, Methyl caproate, Methyl caprylate, Propyl acetate, Amyl acetate, Amyl butyrate, Benzyl salicylate, Dimethyl anthranilate, Ethyl methylphenylglycidate, Ethyl succinate, Isobutyl cinnamate and Terpenyl acetate; Essential Oils such as Jasmine absolute, Rose absolute, Orris absolute, Lemon essential oil and Vanilla; lactones, sulfides, e.g., methyl sulfide and other materials such as Maltol and Citral, as well as natural raspberry oil.

The specific flavoring adjuvants selected for use may be either solid or liquid, depending upon the desired physical form of the ultimate product, i.e., foodstuff, whether simulated or natural, and should, in any event, be capable of providing an environment in which the methylthioionene derivatives can be dispersed or admixed to provide a homogeneous medium. In addition, selection of one or more adjuvants, as well as the quantities thereof, will depend upon the precise organoleptic raspberry character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of methylthioionene derivatives employed in a particular instance can vary over a relatively wide range whereby its desired organoleptic effects (having reference to the nature of the product) are achieved. All parts and percentages given herein are by weight unless otherwise specified. Thus, correspondingly greater amounts would be necessary in those instances wherein the ultimate food composition to be flavored is relatively bland to the taste, whereas relatively minor quantities may suffice for the purposes of enhancing the composition merely deficient in natural flavor or aroma. Thus, the primary requirement is that amount which is effective, i.e., sufficient to alter the organoleptic characteristics of the parent composition, whether foodstuff per se or flavoring composition. Thus, the use of insufficient quantities of methylthioionene derivatives will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus and with respect to ultimate food compositions, it has been found that quantities of methylthioionene derivatives ranging from a small but effective amount, e.g., 0.02 parts per million up to about 50 parts per million by weight based on total composition are suitable. Concentrations in excess of the maximum quantity stated are not normally recommended since they fail to provide commensurate enhancement of organoleptic properties. In those cases wherein the methylthioionene derivatives are added to the foodstuff as an integral component.

Reaction:

of the flavoring composition, it is, of course, essential that the total quantity of flavoring composition employed be sufficient to yield an effective methylthioionene derivative concentration in the foodstuff product.

Food flavoring compositions prepared in accordance with the present invention preferably contain methylthioionene derivatives in concentrations ranging from about 0.05% up to about 10% by weight based on a total weight of said flavoring composition.

The compositions described herein can be prepared according to conventional techniques well known as typified by cake batters and fruit juices and can be formulated by merely admixing the involved ingredients within the proportions stated in a suitable blender to obtain the desired consistency, homogeneity of dispersion, etc. Accordingly, flavoring compositions in the form of particulate solids can be conveniently prepared by admixing the methylthioionene derivatives with, for example, gum arabic, gum tragacanth, carrageenan and the like and thereafter spray-drying the resultant mixture whereby to obtain the particulate solid product. Prepared flavor mixes in powder form, e.g., a raspberry flavored powder are obtained by mixing dried solid, components, e.g., starch, sugar and the like and methylthioionene derivatives in a dry blender until the requisite degree of uniformity is achieved.

It is presently preferred to combine the methylthioionene derivatives with the following adjuvants:
Parahydroxybenzyl acetone;
Vanillin;
Maltol;
α-Ionone;
β-Ionone;
Isobutyl acetate;
Ethyl butyrate;
Dimethyl sulfide;
Acetic acid;
Acetaldehyde;
4-(2,6,6-trimethyl-1,3-cyclohexadien-1-yl)-2-butanone;
4-(6,6-Dimethyl-2-methylene-3-cyclohexen-1-yl)-2-butanone;
2-(4-Hydroxy-4-methylpentyl)norbornadiene
Dimethyl sulfide;
Dipropyl disulfide;
Propylpropenyl disulfide;
Allyl propenyl disulfide;
Diallyl disulfide; and
Diallyl trisulfide.

The following examples are given to illustrate the embodiments of our invention as it is presently preferred to practice it. It will be understood that these examples are illustrative, and that the invention is not to be considered as restricted thereto except as indicated in the appended claims.

EXAMPLE I

PREPARATION OF THE METHYLTHIO ETHER OF DIHYDRO-α-IONENE

Reaction:

Into a 250 ml reaction flask equipped with stirrer, thermometer and reflux condenser is added 50 ml methylene dichloride. The methylene dichloride is cooled to −15° C. and over a period of one hour, 15 grams of methyl mercaptan is added to the methylene dichloride while maintaining the temperature at −15° C. The resulting mixture is transferred to a Parr bomb previously containing 0.5 grams of para toluene sulfonic acid and 19.5 grams of dihydro-α-ionone having the structure:

The Parr bomb is closed and the contents are heated with shaking to a temperature of 100°–105° C. The Parr bomb is maintained at 100°–105° C., sealed for a period of 12 hours. At the end of the 12 hours, the Parr bomb contents are cooled and the Parr bomb is opened and the contents are fractionally distilled yielding the compound having the structure:

as confirmed by GLC, NMR, IR and mass spectral analyses. The compound having the structure:

has a raw green bean and raw carrot aroma and taste profile at 10 ppm.

Figure 1:
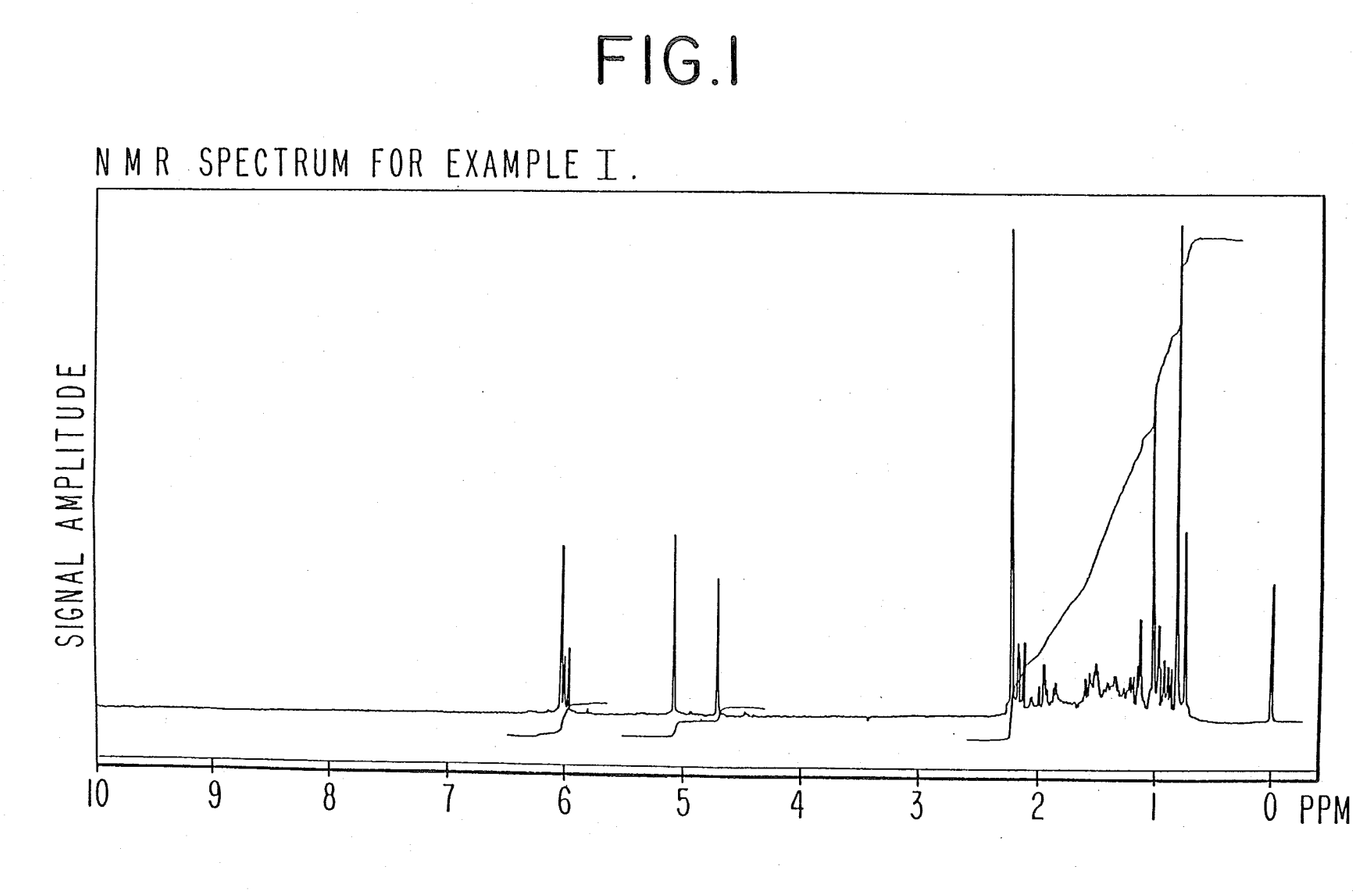

FIG. 1 is the NMR spectrum for the compound having the structure:

(Conditions: Field strength: 100 MHz; Solvent: CFCl₃).

EXAMPLE II

PREPARATION OF THE DIMETHYL MERCAPTAL OF α-IONONE

Reaction:

Into a 500 ml reaction flask equipped with stirrer, thermometer, reflux condenser and cooling coils are placed 200 ml methylene dichloride; 0.5 grams para toluene sulfonic acid; 38.46 grams of α-ionone having the structure:

and 0.15 ml concentrated sulfuric acid (93%). Over a period of four hours while maintaining the reaction temperature at 0° C., 48 grams of methyl mercaptan is added to the reaction mass. At that point in time that the addition of the methyl mercaptan is complete, the reaction mass is stirred while maintaining the temperature of the reaction mass at 25° C. for a period of eight hours. At the end of the eight hour period, the reaction mass is fractionally distilled yielding a mixture of compounds having the structures:

The mixture of compounds having the structures:

is separated using preparative GLC separation techniques.

The compound having the structure:

has an aesthetically pleasing cabbage aroma and taste profile at 2 ppm. The compound having the structure:

has a minty and raspberry aroma and taste profile at 1 ppm.

Figure 2:
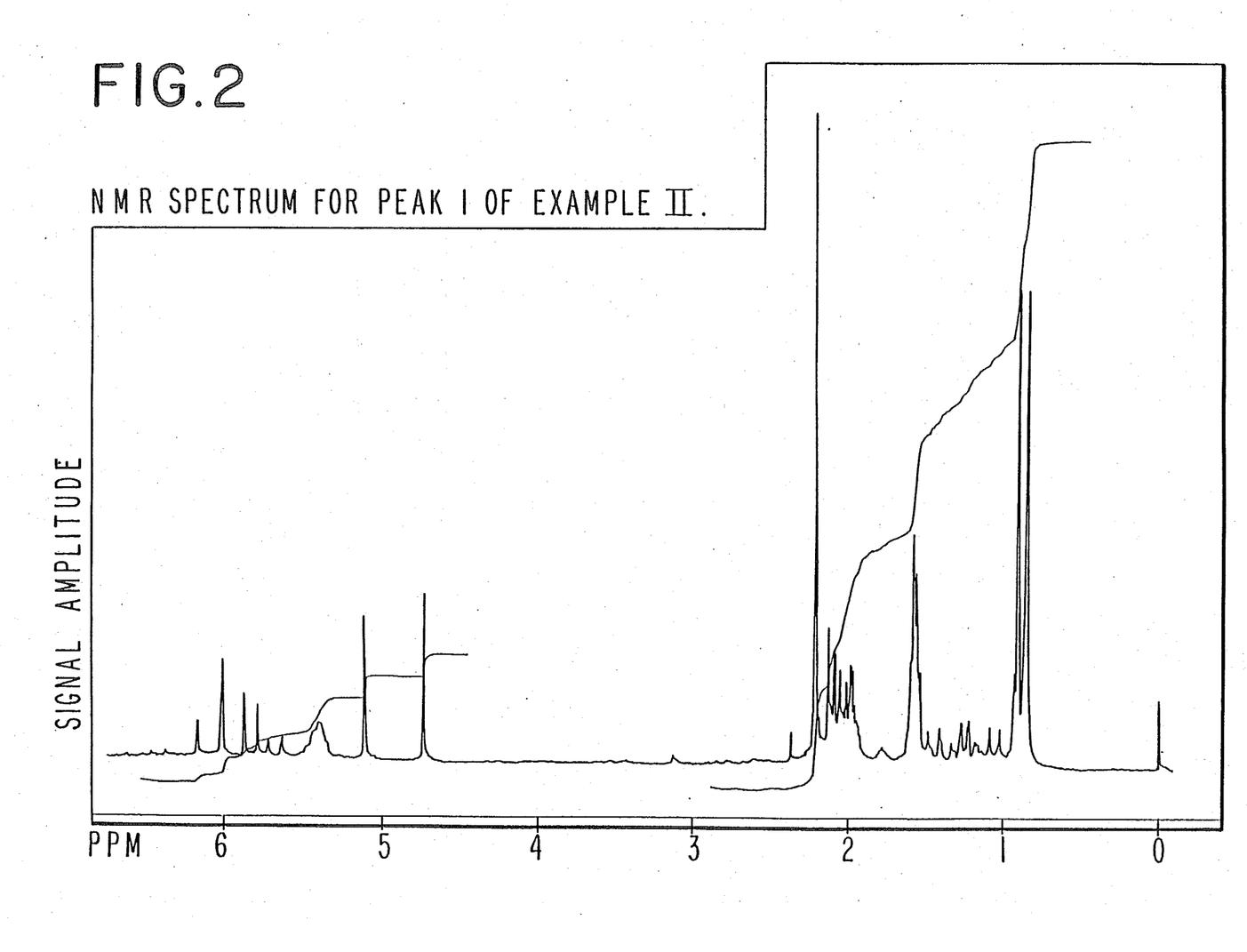

FIG. 2 is the NMR spectrum for the compound having the structure:

(Conditions: Field strength: 100 MHz; Solvent: CFCl₃).

Figure 3:
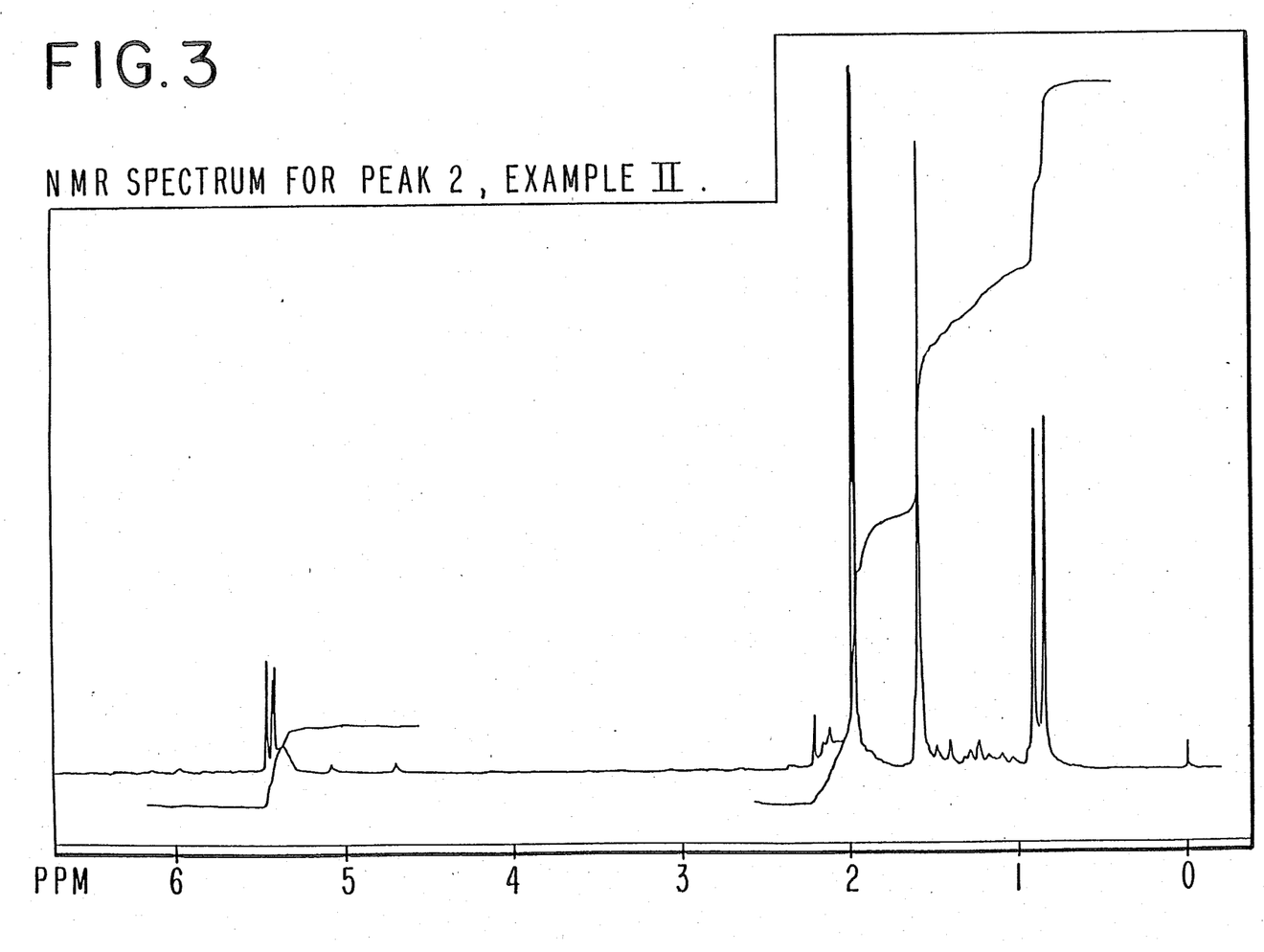

FIG. 3 is the NMR spectrum for the compound having the structure:

(Conditions: Field strength: 100 MHz: Solvent: CFCl₃).

EXAMPLE III

The following formulation is prepared:

| Ingredients | Parts by Weight |
|---|---|
| para-hydroxybenzyl acetone | 4 |
| vanillin | 1 |
| maltol | 2 |
| α-ionone (10% in propylene glycol) | 2 |
| isobutyl acetate | 20 |
| ethyl butyrate | 5 |
| dimethyl sulfide | 1 |
| acetic acid | 10 |
| acetaldehyde | 15 |
| propylene glycol | 940 |

The compound having the structure:

prepared according to Example II is added to a portion of the above formulation at the rate of 2%. The formulation with the compound having the structure:

is compared with the formulation without said compound at the rate of 0.01% (100 ppm) in water by a blind bench panel of five members not associated with the inventive entity. The flavor containing the compound having the structure:

is determined to have the aroma and taste of full ripened raspberries with a minty nuance and a seedy, raspberry kernel note. These notes are not present in the formulation without the compound having the structure:

The formulation is further enhanced by the addition at the level of 1 ppm of 2-(4-hydroxy-4-methylpentyl)norbornadiene prepared according to U.S. Pat. No. 3,911,028.

EXAMPLE IV

The following mixture is prepared:

| Ingredients | Parts by Weight |
|---|---|
| Natural Raspberry Concentrate Juice | 2½% |
| Water | 85% |
| Sugar syrup (37.5° Baume) | 12½% |

The fresh, ripened raspberry, minty, seedy and raspberry kernel note of this raspberry juice is imparted in increased strength by the addition of the compound having the structure:

at the rate of 2–20 parts per million.

EXAMPLE V

To the raspberry formulation of Example III, the compound having the structure:

at the rate of 4% is added. The material is then called the "test composition". The raspberry formulation without the compound having the structure:

is called the "control composition".

The test and control compositions are added to the food products described hereinafter in the proportions shown for 10 kilograms of material to be flavored:

| | |
|---|---|
| Pudding | 5–10 grams (0.15–.1%) |
| Cooked sugar | 15–20 grams (.15–2%) |

Cooked sugar—100 ml of sugar syrup (prepared by dissolving 1 kilogram of sucrose in 600 ml of water) and 20 grams of glucose are mixed together and slowly heated to 145° C. The flavor is added and the mass allowed to cool and harden. Pudding—To 500 ml of warmed milk are added with stirring a mixture of 60 grams sucrose and 3 grams of pectin. The mixture is boiled for a few seconds and the flavor is added. The mixture was allowed to cool.

The finished foodstuff samples are tested by a panel of trained persons who express their views about the flavor of the samples. All members of the panel prefer the test samples having a more distinguished ripened, fresh raspberry aroma with a taste of freshly picked ripe raspberries and its seedy kernel and minty note.

EXAMPLE VI

The compound having the structure:

produced according to Example II is added at the level of 15 ppm (in a propylene glycol solution containing 0.1% of the compound) to 7.3 grams of soup base consisting of:

| Ingredient | Quantity (Parts/100 total) |
|---|---|
| Fine ground sodium chloride | 35.62 |
| Hydrolyzed vegetable protein (4 BE:Nestle's) | 27.40 |
| Monosodium glutamate | 17.81 |
| Sucrose | 10.96 |
| Beef fat | 5.48 |
| Sethness caramel color (powder B & C) | 2.73 |

The resulting mixture is added to 12 ounces of boiling water to create a soup having an excellent cabbage and hydrolyzed vegetable protein-like aroma and taste profile with intense cabbage nuances and an overall good roast beef character.

When the compound having the structure:

prepared according to Example I is added to the soup base at the level of 5 ppm, the soup base has an increased fresh vegetable aroma and taste profile reminiscent of fresh carrots and freshly cut raw green beans.

EXAMPLE VII

An omelet is prepared using a bland margarine and dried prepared eggs (as utilized in an army field kitchen platter). The omelet is split up into two portions. To the first portion nothing is added. To the second portion the compound having the structure:

prepared according to Example I is added. The compound having the structure:

is added at the level of 5 ppm to the omelet during the cooking of same with the bland margarine. The compound having the structure:

adds to this bland omelet an interesting, fine herbs omelet-like aroma and taste profile unanimously preferred by a bench panel (blind panel) of five members not associated with the inventive entity of the instant invention.

What is claimed is:

1. The methylthioionene derivative having the structure:

2. The methylthioionene derivative having the structure:

3. The methylthioionene derivative having the structure:

* * * * *